US00PP20030P2

(12) United States Plant Patent
Konst

(10) Patent No.: US PP20,030 P2
(45) Date of Patent: May 26, 2009

(54) ***ALSTROEMERIA* PLANT NAMED 'KONESERT'**

(50) Latin Name: *Alstroemeria hybrida*
Varietal Denomination: Konesert

(75) Inventor: Johannes Wilhelmus Maria Konst, Nieuwveen (NL)

(73) Assignee: Könst Breeding B.V., Nieuwveem (NL)

( * ) Notice: Subject to any disclaimer, the term of this patent is extended or adjusted under 35 U.S.C. 154(b) by 0 days.

(21) Appl. No.: 12/154,244

(22) Filed: May 21, 2008

(51) Int. Cl.
*A01H 5/00* (2006.01)

(52) U.S. Cl. ..... Plt./309

(58) Field of Classification Search ..... Plt./309
See application file for complete search history.

*Primary Examiner*—Annette H Para
(74) *Attorney, Agent, or Firm*—C. A. Whealy

(57) ABSTRACT

A new and distinct cultivar of *Alstroemeria* plant named 'Konesert', characterized by its compact and mounding plant habit; sturdy and strong plants; vigorous growth habit; light yellow-colored flowers; and good garden performance.

2 Drawing Sheets

Botanical designation: *Alstroemeria hybrida.*
Cultivar denomination: 'Konesert'.

BACKGROUND OF THE INVENTION

The present invention relates to a new and distinct cultivar of *Alstroemeria* plant, botanically known as *Alstroemeria hybrida,* grown typically as a potted garden *Alstroemeria,* and hereinafter referred to by the name 'Konesert'.

The new *Alstroemeria* is a product of a planned breeding program conducted by the Inventor in Nieuwveen, The Netherlands. The objective of the breeding program is to create new compact potted garden *Alstroemeria* cultivars that flower early and freely and have attractive foliage and flower coloration.

The new *Alstroemeria* originated from a cross-pollination made by the Inventor in Nieuwveen, The Netherlands on Jun. 5, 2000, of the *Alstroemeria hybrida* 'Koserin', disclosed in U.S. Plant Pat. No. 15,996, as the female, or seed, parent with a proprietary *Alstroemeria hybrida* selection identified as code number 5328-5, not patented, as the male, or pollen, parent. The new *Alstroemeria* was discovered and selected by the Inventor as a flowering plant from within the progeny of the stated cross-pollination in a controlled greenhouse environment in Nieuwveen, The Netherlands on Apr. 21, 2004.

Asexual reproduction of the new *Alstroemeria* by root divisions in a controlled greenhouse environment in Nieuwveen, The Netherlands since Apr. 29, 2004, has shown that the unique features of this new *Alstroemeria* are stable and reproduced true to type in successive generations.

SUMMARY OF THE INVENTION

The new *Alstroemeria* has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Konesert'. These characteristics in combination distinguish 'Konesert' as a new and distinct cultivar of *Alstroemeria:*

1. Compact and mounding plant habit.
2. Sturdy and strong plants.
3. Vigorous growth habit.
4. Light yellow-colored flowers.
5. Good garden performance.

Plants of the new *Alstroemeria* can be compared to plants of the female parent, 'Koserin'. Plants of the new *Alstroemeria* differ from plants of 'Koserin' in the following characteristics:

1. Plants of the new *Alstroemeria* are more compact than plants of 'Koserin'.
2. Plants of the new *Alstroemeria* and 'Koserin' differ in flower color as plants of 'Koserin' have pink and yellow-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* have larger flowers than plants of the male parent selection.
3. Plants of the new *Alstroemeria* and the male parent selection differ in flower color as plants of the male parent selection have bright yellow-colored flowers.

Plants of the new *Alstroemeria* can be compared to plants of the *Alstroemeria hybrida* 'California', not patented. In side-by-side comparisons conducted in Nieuwveen, The Netherlands, plants of the new *Alstroemeria* differed fom plants of 'California' in the following characteristics:

1. Plants of the new *Alstroemeria* were more compact than plants of 'California'.
2. Plants of the new *Alstroemeria* had smaller flowers than plants of 'California'.
3. Plants of the new *Alstroemeria* had lighter yellow-colored flowers than plants of 'California'.

BRIEF DESCRIPTION OF THE PHOTOGRAPHS

The accompanying colored photographs illustrate the overall appearance of the new *Alstroemeria,* showing the colors as true as it is reasonably possible to obtain in colored reproductions of this type. Colors in the photographs may differ slightly from the color values cited in the detailed botanical description which accurately describe the colors of the new *Alstroemeria*.

The photograph on the first sheet comprises a side perspective view of a typical flowering plant of 'Konesert' grown in a container.

The photograph on the second sheet is a close-up view of a typical flowering stem of 'Konesert'.

DETAILED BOTANICAL DESCRIPTION

The aforementioned photographs and following observations and measurements describe plants of the new *Alstroemeria* grown in Nieuwveen, The Netherlands during the spring and summer in a glass-covered greenhouse in containers. During the production of the plants, day temperatures ranged from 6° C. to 30° C. and night temperatures ranged from 2° C. to 16° C. Plants used for the photographs and description were 26 weeks from planting. Color references are made to The Royal Horticultural Society Colour Chart, 2001 Edition, except where general terms of ordinary dictionary significance are used.

Botanical classification: *Alstroemeria hybrida* 'Konesert'.

Parentage:

*Female, or seed, parent.*—*Alstroemeria hybrida* 'Koserin', disclosed in U.S. Plant Pat. No. 15,996.

*Male or pollen parent.*—Proprietary *Alstroemeria hybrida* selection identified as code number 5328-5, not patented.

Propagation:

*Type.*—By root divisions.

*Root description.*—Fibrous, thin, color, close to 162D.

*Rhizome description.*—Shape: Elongate; rounded. Length: About 5 cm. Diameter: About 6 mm. Texture: Smooth. Color: Close to 162D.

Plant description:

*Plant habit.*—Compact and mounded, freely branching, bushy appearance. Sturdy and strong plants; vigorous growth habit.

*Plant height.*—About 25 cm.

*Plant diameter* (*area of spread*). About 50 cm.

Stem description:

*Aspect.*—Mostly upright to somewhat outwardly spreading.

*Internode length.*—About 0.5 cm to 2.3 cm.

*Strength.*—Strong, sturdy.

*Textured.*—Smooth, glabrous.

*Color.*—Close to 152B; spotted with close to 166B; towards the apex, close to 166B.

Foliage description:

*Arrangement.*—Alternate; below the peduncles in a single whorl; sessile.

*Length.*—About 12.5 cm.

*Width.*—About 2.5 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing foliage, upper surface: Close to 138A. Developing foliage, lower surface: Close to 138B. Fully expanded foliage, upper surface: Close to 137A; venation, close to 144C. Fully expanded foliage, lower surface: Close to 137C; venation, close to 139B.

Flower description:

*Flower type and habit.*—Single cup-shaped flowers arranged in compound umbels. Flowers face upright or outwardly. Perianth segments separate. Freely flowering habit; about three to eight flowers per inflorescence; about 30 to 60 flowers develop per plant.

*Natural flowering season.*—Flowering continuous from the late spring until frost in The Netherlands.

*Fragrance.*—None detected.

*Flower longevity on the plant.*—About one to three weeks; flowers not persistent.

*Flower buds.*—Length: About 4 cm. Diameter: About 1.7 cm. Shape: Ovoid. Color: Close to N167A; towards the apex, close to 138A.

*Umbel height.*—About 9.5 cm.

*Umbel diameter.*—About 12.5 cm.

*Flower diameter.*—About 4.3 cm.

*Flower depth* (*height*).—About 5.7 cm.

*Perianth.*—Arrangement: Six arranged in two whorls, each whorl with two lateral and one median segments. Size, inner perianth: Length, lateral segments. About 5.5 cm. Width, lateral segments: About 1.5 cm. Length, median segment: About 4.6 cm. Width, median segment: About 1.5 cm. Size, outer perianth: Length, lateral segments: About 4.6 cm. Width, lateral segments: About 2.5 cm. Length, median segment: About 5.2 cm. Width, median segment: About 2.5 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner and outer perianths, lateral and median segments: Attenuate. Margin, inner perianth, lateral and median segments: Entire. Margin, outer perianth, lateral and median segments: Slightly crenate. Texture, inner and outer perianths, lateral and median segments: Smooth, glabrous. Color, inner perianth: When opening, lateral and median segments, upper surface: Close to 1B; towards the apex, close to 1D and 143B; stripes, close to 187A. When opening, lateral and median segments, lower surface: Close to 1B; towards the apex, close to 1D. Fully opened, lateral segments, upper surface: Close to 7A; towards the apex, close to 13C and 143B; stripes, close to 187A. With development, color becoming closer to 7B; towards the apex, close to 155C. Fully opened, median segment, upper surface: Close to 3C; towards the apex, close to 11D and 143B; stripes, close to 187A. With development, color becoming closer to 7B; towards the apex, close to 155C. Fully opened, lateral segments, lower surface: Close to 11A; towards the apex, close to 11D. Fully opened, median segment, upper surface: Close to 11B; towards the apex, close to 11D. Color, outer perianth: When opening, lateral and median segments, upper and lower surfaces: Close to 11C; towards the apex, close to 1B and 143B. Fully opened, lateral segments, upper surface: Close to 11C; towards the apex, close to 143B. With development, color becoming closer to 155C; towards the apex, close to 143C. Fully opened, median segment, upper surface: Close to 11B;

towards the apex, close to 155C and 143B. With development, color becoming closer to 155C; towards the apex, close to 143C. Fully opened, lateral and median segments, lower surface: Close to 48D; towards the margins, close to 11B; towards the apex, close to 155C.

*Pedicels.*—Length: About 4.4 cm. Diameter: About 2.5 mm. Strength: Strong. Angle: About 30° C. from vertical. Texture: Smooth, glabrous. Color: Close to 144A covered with spots, close to 187A.

*Reproductive organs.*—Stamens: Quantity per flower: Six. Anther shape: Oval. Anther size: About 7 mm by 3 mm. Anther color: Close to 199A. Pollen amount: Abundant. Pollen color: Close to N189A. Pistils: Quantity per flower: One. Pistil length: About 4.5 cm. Style length: About 3.6 cm. Style color: Close to 62D. Stigma color: Close to 62D. Ovary color: Close to 144A; with development, color becoming closer to 166A.

*Fruits.*—Length: About 7 mm. Diameter: About 6 mm. Color: Close to 166A.

Disease/pest resistance: Plants of the new *Alstroemeria* have not been observed to be resistant to pathogens and pests common to *Alstroemeria.*

Garden performance: Plants of the new *Alstroemeria* have been observed to have good garden performance and to tolerate wind, rain and temperatures ranging from about 2° C. to about 30° C.

It is claimed:

1. A new and distinct *Alstroemeria* plant named 'Konesert' as illustrated and described.

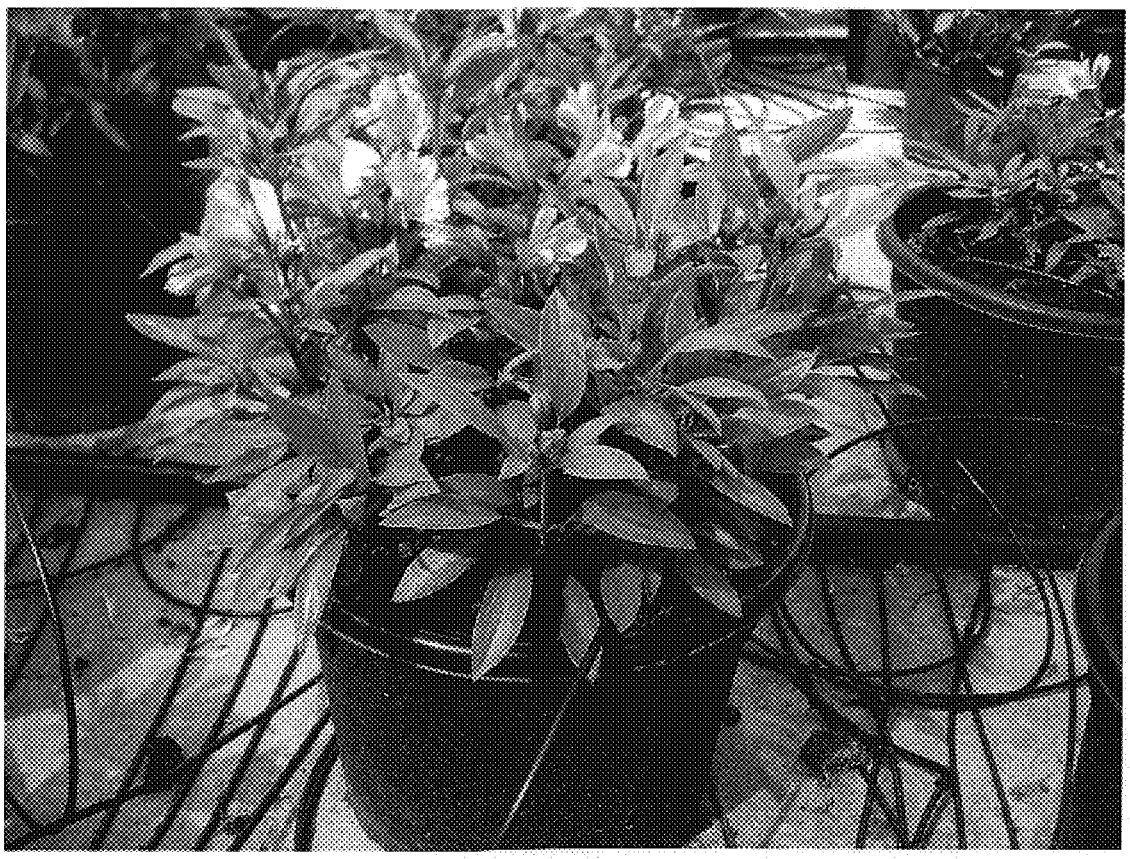

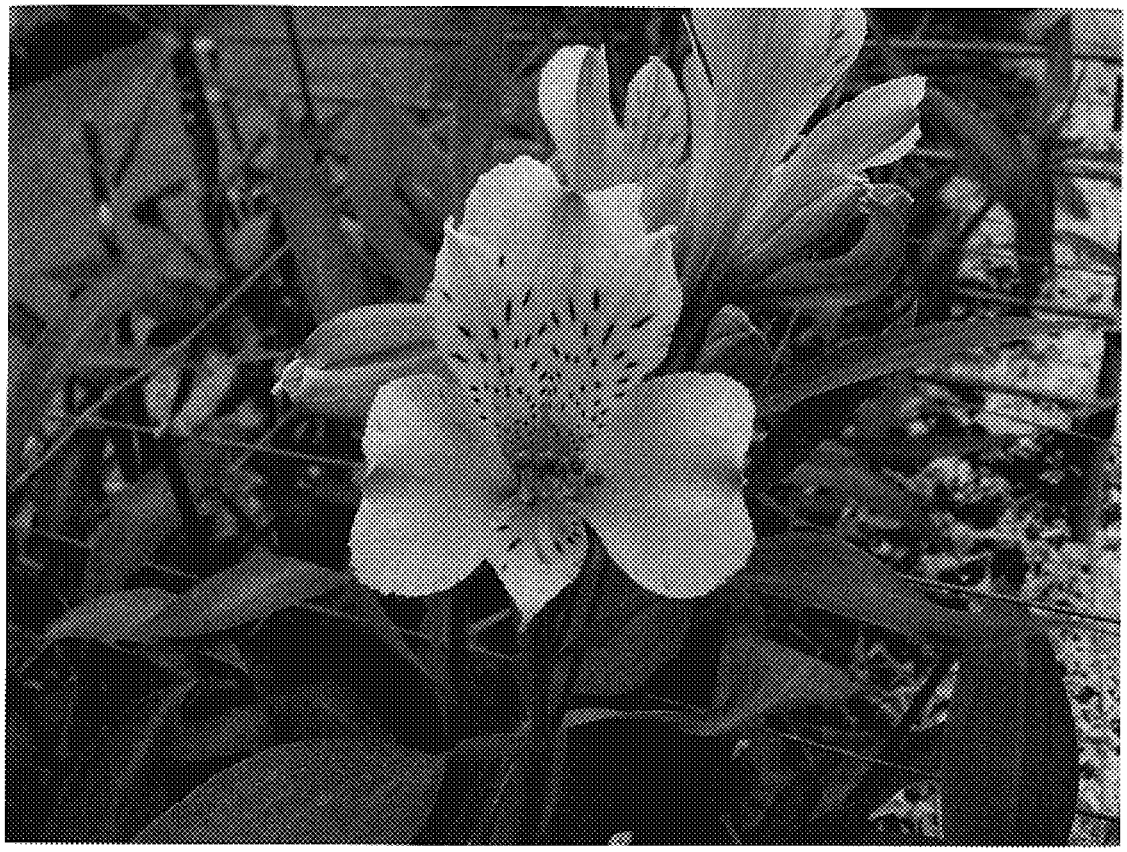

* * * * *